United States Patent [19]

Isak et al.

[11] Patent Number: 5,504,249

[45] Date of Patent: Apr. 2, 1996

[54] PREPARATION OF O-CHLOROMETHYLBENZOYL CHLORIDES

[75] Inventors: Heinz Isak, Böhl-Iggelheim; Herbert Bayer, Mannheim; Michael Keil, Freinsheim; Thomas Wettling, Limburgerhof, all of Germany

[73] Assignee: BASF Aktiengesellschaft, Ludwigshafen, Germany

[21] Appl. No.: 414,491

[22] Filed: Mar. 31, 1995

[30] Foreign Application Priority Data

Apr. 11, 1994 [DE] Germany ............... 44 12 316.7

[51] Int. Cl.⁶ .................................... C02C 51/58
[52] U.S. Cl. ............................. 562/861; 562/862
[58] Field of Search ........................ 562/861, 862

[56] References Cited

U.S. PATENT DOCUMENTS

| | | | |
|---|---|---|---|
| 2,548,161 | 4/1951 | Jansen et al. ................. | 562/862 |
| 2,778,852 | 1/1957 | Adam et al. . | |
| 3,418,365 | 12/1968 | Gustafson .................... | 562/862 |
| 4,764,309 | 8/1988 | Deckers et al. . | |
| 4,871,484 | 10/1989 | Fiege et al. ................... | 562/862 |

FOREIGN PATENT DOCUMENTS

| | | |
|---|---|---|
| 860207 | 7/1949 | Germany . |
| 2751134 | 5/1979 | Germany . |
| 3624258 | 7/1986 | Germany . |
| 3927146 | 2/1991 | Germany . |
| 4223382 | 10/1994 | Germany . |
| 8605786 | 10/1986 | WIPO . |

OTHER PUBLICATIONS

Chemical Abstract 106 (1987) 84, 307y.

*Primary Examiner*—Paul J. Killos
*Attorney, Agent, or Firm*—Keil & Weinkauf

[57] ABSTRACT

A process for preparing o-chloromethylbenzoyl chlorides of the formula I where
m is 0 or an integer from 1 to 4 and
X is halogen or C-organic radicals,
entails reacting a corresponding lactone of the formula II

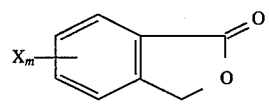

with thionyl chloride in the presence of a catalyst.

7 Claims, No Drawings

PREPARATION OF O-CHLOROMETHYLBENZOYL CHLORIDES

The present invention relates to a process for preparing o-chloromethylbenzoyl chlorides of the formula I

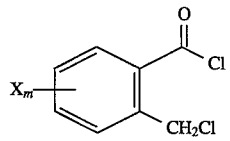

where
m is 0 or an integer from 1 to 4 and
X is halogen or C-organic radicals,
by reacting a corresponding lactone of the formula II

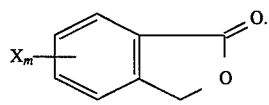

The reaction of aliphatic lactones with phosgene in the presence of pyridine (US-A-2,778,852), quaternary ammonium salts (DE-A 36 24 258) or phosphine oxides (DE-A 39 27 146) as catalyst is disclosed in the literature. In addition, the conversion of phthalide into o-chloromethylbenzoyl chloride using phosphorus pentachloride in the presence of zinc(II) chloride is described [CA 106 (1987) 84, 307y].

There are objections to both phosgene and phosphorus pentachloride in terms of industrial preparation of corresponding carbonyl chlorides because of their toxicity or the toxicity of the breakdown parts thereof. Phosgenation as described, for example, in EP-A 583 589 takes place at 170° C. This means that a very costly cooling to −70° C. is needed to condense the phosgene out of the off-gas. In addition, the safety requirements for such products are so great that new capital expenditure cannot be economic. Furthermore, in practice the excess of phosgene to be used in phosgenations in industrial plants is, as a rule, distinctly greater than the excess to be used on the laboratory scale. Transport of products from the phosgenation is also subject to strict safety requirements in respect of the limits on phosgene, so that it is often necessary to drive out residual amounts of phosgene using nitrogen, which is costly.

As a rule, use of phosphorus pentachloride on the industrial scale is unacceptable owing to the considerable wastewater problems due to the formation of phosphorus-containing waste products, eg. phosphoric acid and esters thereof, as pollutants of the wastewater.

It is an object of the present invention to prepare halogenated carbonyl chlorides by a method which does not have the above disadvantages and can be used on the industrial scale.

We have found that this object is achieved by preparing o-chloromethylbenzoyl chlorides of the formula I by reacting the corresponding lactones of the formula II with thionyl chloride in the presence of a catalyst.

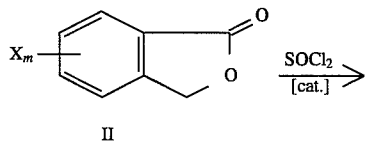

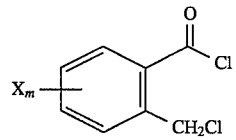

The reaction generally requires a minimum temperature of 80° C., and the reaction rate increases as the temperature rises. Decomposition increases above 300° C., and this markedly reduces the product yield above 350° C.

The reaction is therefore normally carried out at from 80° C. to 240° C., preferably 130° C. to 200° C., in particular 160° C. to 190° C.

Particularly suitable catalysts are organic nitrogen compounds, eg. nitrogen-containing aromatic or aliphatic heterocycles such as pyrazole, imidazole, pyridine, pyrimidine, pyrazine, indole, quinoline, piperidine, piperazine and morpholine, and corresponding alkyl-substituted heterocycles (eg. 1-methylimidazole, methyl- or dimethylpyridines, 1-decylimidazole, N-methylpiperidine, N,N'-dimethylpiperazine, N-methylmorpholine), tertiary aliphatic or aromatic amines, eg. tri($C_1$–$C_6$-alkyl)amines (trimethylamine, triethylamine, tripropylamine, tri(1-methylethyl)amine, tributylamine, tri(1-methylpropyl)amine, tri(2-methylpropyl)amine, N,N-dimethylaniline or amines which have two or three different alkyl radicals with 1 to 6 carbon atoms or two identical or different alkyl radicals with 1 to 6 carbon atoms or two identical or different alkyl radicals with 1 to 6 carbon atoms and an aryl radical, eg. phenyl or benzyl), and corresponding quaternary ammonium salts, in particular quaternary ammonium chlorides (eg. tetramethylammonium chloride, tetrabutylammonium chloride, benzyltrimethylammonium chloride), N,N,N',N'-tetra($C_1$–$C_6$-alkyl/aryl)ureas or -guanidines (eg. N,N,N',N'-tetramethylurea, N,N,N',N'-tetrabutylurea, N,N'-dimethyl-N,N'-diphenylurea, tetramethylguanidine, tetraphenylguanidine) and, in particular, N,N-di($C_1$–$C_6$-alkyl/aryl)formamides (eg. dimethylformamide, diethylformamide, dipropylformamide, di(1-methylethyl)formamide, dibutylformamide, di(1-methylpropyl)formamide, di(2-methylpropyl)formamide, methylphenylformamide).

The amount of catalysts should not be below 0.1 mol % based on the lactone. In general, the reaction rate increases as the amount of catalyst increases. However, as a rule, no noticeable improvement is achieved with amounts above about 25 mol%.

The catalyst is therefore normally added in amounts of 0.1–25 mol %, preferably 0.15–10 mol %, in particular 0.5–5 mol %, based on the amounts of lactone II.

The thionyl chloride can simultaneously act as solvent for the lactone and, in such a case, is used in an appropriate excess which depends on the dissolving behavior of the lactone. It is not normally necessary for the excess to be more than 10 mol of thionyl chloride per mol of lactone II. If the reaction is carried out in an inert solvent, smaller amounts of thionyl chloride are used.

The thionyl chloride is normally used in amounts of 0.8–10 mol, preferably 0.8–5 mol, in particular 1–2 mol, per mol of lactone II.

The reaction can be carried out under atmospheric or superatmospheric pressure (preferably 0.01–50 bar, in particular 0.1–5 bar gauge pressure).

A reaction under atmospheric pressure is particularly advantageously carried out in the presence of hydrogen chloride or of a compound which liberates hydrogen chloride from thionyl chloride. This addition considerably increases the reaction rate and improves the conversion. A particularly suitable compound which liberates hydrogen chloride is water.

In the case of reaction in the presence of hydrogen chloride it is possible to use 5–100 mol % of hydrogen chloride based on lactone II, preferably 10–50 mol %, in particular 20–40 mol %. On the one hand, the use of larger amounts of hydrogen chloride is disadvantageous for economic reasons and, on the other hand, the use of larger amounts may lead to unwanted stripping effects, ie. on boiling, large amounts of thionyl chloride are carried over into the condenser. Such effects would cause losses of yield.

When water is used as compound which liberates hydrogen chloride, normally 0.5–50% by weight, preferably 0.5–25% by weight, in particular 1–25% by weight, are used.

The process according to the invention is normally carried out by gradually adding the required amount of thionyl chloride to a mixture of lactone II and catalyst, which may contain an inert solvent, at the reaction temperature. Thionyl chloride which distils out can be returned to the reaction.

When hydrogen chloride or a compound which liberates hydrogen chloride is additionally used, the addition takes place simultaneously with but separately from the thionyl chloride.

When thionyl chloride is used as solvent it is possible to mix the lactone II with thionyl chloride and, at 120°–170° C., where appropriate to add water or a compound which liberates hydrogen chloride.

Inert solvents (diluents) which can be used in principle are all organic solvents which are inert under the reaction conditions and whose boiling point permits the required reaction temperature. Examples thereof are high-boiling hydrocarbons such as cumene, liquid paraffin and naphthalene or else chlorinated hydrocarbons such as dichlorobenzene and trichlorobenzene.

After the reaction is complete, excess thionyl chloride and, where appropriate, solvent are removed by distillation (where appropriate under reduced pressure). The products can be obtained pure by fractional distillation.

The process according to the invention is suitable for preparing o-chloromethylbenzoyl chlorides of the formula I

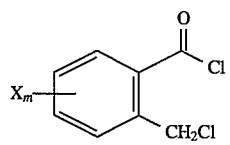

where
m is 0 or an integer from 1 to 4, and
X is halogen or C-organic radicals, it being possible for the group X to be different when m is greater than 1.

By halogen is meant in this case fluorine, chlorine, bromine and iodine, preferably fluorine, chlorine and bromine, especially fluorine and chlorine. Suitable C-organic radicals are in principle all radicals which are inert under the reaction conditions.

Examples thereof are:

- alkyl groups, eg. with 1–20 carbon atoms, preferably straight-chain or branched alkyl groups with 1–8, in particular 1–6, carbon atoms,
- alkenyl groups, eg. with 2–20 carbon atoms, preferably straight-chain or branched alkenyl groups with 2–8, in particular 2–6, carbon atoms;
- alkynyl groups, eg. with 2–20 carbon atoms, preferably straight-chain or branched alkynyl groups with 2–8, in particular 2–6, carbon atoms, it being possible for the abovementioned groups in turn to be partially or completely halogenated and/or to carry further radicals which are stable under the reaction conditions (eg. cycloalkyl, aryl and heteroaryl).

Other examples of C-organic radicals are:

- cycloalkyl groups, eg. with 3–10 carbon ring members, preferably $C_3$–$C_7$-cycloalkyl groups;
- aryl groups, eg. phenyl, naphthyl or anthryl, it being possible for the abovementioned cyclic radicals in turn to be partially or completely halogenated and/or to carry further radicals which are stable under the reaction conditions (eg. alkyl, alkenyl, alkynyl, cycloalkyl, aryl or heteroaryl).

C-Organic radicals also mean in the case where m is 2 or above

- alkylene chains with 1–6 carbon atoms (preferably 1, 3 or 4 carbon atoms) or
- alkenylene chains with 4 carbon atoms (eg. 1-butene-1,4-diyl, 2-butene-1,4-diyl or 1,3-butadiene-1,4-diyl) which are bonded to adjacent positions of the phenyl ring, it being possible for these radicals in turn to be partially or completely halogenated and/or to carry further radicals which are stable under the reaction conditions (eg. alkyl, alkenyl, alkynyl, cycloalkyl, aryl or heteroaryl).

The o-chloromethylbenzoyl chlorides obtainable by the process according to the invention are valuable intermediates for the synthesis of dyes, drugs and, in particular, crop protection agents.

EXAMPLES OF THE PROCESS

General Method x g of phthalide and 15 mol % of the catalyst were introduced into a stirred reactor with cooling and means for introducing hydrogen chloride or water. The mixture was heated to 160°–180° C. (internal temperature) and, at this temperature, y g of thionyl chloride and about 5–10 l/h hydrogen chloride (gaseous) were introduced over the course of t hours. Thionyl chloride distilling out during the reaction was condensed out and returned to the reaction.

After the reaction was complete, the mixture was kept at the reaction temperature for a further hour before the excess thionyl chloride was removed by distillation. The pure products were obtained by fractional distillation.

Details of the experiments are compiled in the following table (Examples 1 to 5).

TABLE

| Example | Phthalide x [g] | [mol] | Catalyst | Amount [g] | [mol %] | Thionyl chloride [g] | [mol] | R.T. t [h] | Temp. [°C.] | Yield [g] | [%] |
|---|---|---|---|---|---|---|---|---|---|---|---|
| 1 | 134 | 1 | Dimethyl-formamide | 14.6 | 0.2 | 150 | 1.25 | 3 | 170 | 145.5 | 77 |
| 2 | 134 | 1 | Di-sec-butyl-formamide | 31.4 | 0.2 | 155 | 1.30 | 3 | 170 | 122.8 | 65 |
| 3 | 134 | 1 | Dimethyl-formamide | 3.65 | 0.05 | 151 | 1.25 | 4 | 165–170 | 111.5 | 59 |

TABLE-continued

| Ex- | Phthalide | | Catalyst | Amount | | Thionyl chloride | | R.T. | Temp. | Yield | |
|---|---|---|---|---|---|---|---|---|---|---|---|
| ample | x [g] | [mol] | | [g] | [mol %] | [g] | [mol] | t [h] | [°C.] | [g] | [%] |
| 4 | 134 | 1 | Dimethyl-formamide | 14.6 | 0.2 | 170 | 1.42 | 3 | 165 | 168.2 | 89 |
| 5 | 134 | 1 | Dimethyl-formamide in 500 ml 1,2-dichloro-benzene | 14.6 | 0.2 | 150 | 1.25 | 5 | 165–170 | 9.2 | 4.9 |

EXAMPLE 6

134 g (0.1 mol) of phthalide and 0.1 mol % of catalyst (dimethylformamide) were dissolved in 119 g (0.1 mol) of thionyl chloride in a stirred reactor (autoclave with stirrer) with cooling and means for introducing water or hydrogen chloride, and heated to 160° C. while maintaining the pressure. The mixture was stirred at this temperature for 8 hours and then cooled. The mixture was subsequently fractionally distilled. The thionyl chloride which was removed was reused.

Yield: 15.8 g (83.7% of 2-chloromethylbenzoyl chloride)
Boiling point 120°–125° C. (under 10 mbar)

We claim:

1. A process for preparing o-chloromethylbenzoyl chlorides of the formula I

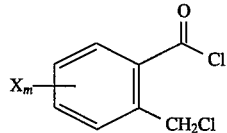

where
m is 0 or an integer from 1 to 4 and
X is halogen or C-organic radicals,
which comprises reacting a corresponding lactone of the formula II

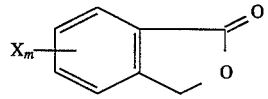

with thionyl chloride in the presence of a catalyst.

2. A process as claimed in claim 1, wherein the reaction is carried out at from 80° C. to 240° C.

3. A process as claimed in claim 1, wherein organic nitrogen compounds are used as catalyst.

4. A process as claimed in claim 1, wherein 0.5–25 mol % of a catalyst are used, based on the lactone II.

5. A process as claimed in claim 1, wherein 0.8–10 mol of thionyl chloride are used per mol of the lactone II.

6. A process as claimed in claim 1, wherein the reaction is carried out in the presence of 5–100% by weight of hydrogen chloride, or of a compound which liberates hydrogen chloride from thionyl chloride, based on the thionyl chloride.

7. A process as claimed in claim 1, wherein the reaction is carried out in the presence of up to 5% by weight of water based on the thionyl chloride.

* * * * *